United States Patent
Gotz et al.

(10) Patent No.: US 10,725,009 B2
(45) Date of Patent: Jul. 28, 2020

(54) OIL MEASUREMENT DEVICE AND METHOD FOR MONITORING AN OIL SITUATED IN A TANK

(71) Applicant: Testo SE & Co. KGaA, Lenzkirch (DE)

(72) Inventors: Meinrad Gotz, Bonndorf (DE); Markus Munzer, Hufingen (DE)

(73) Assignee: Testo SE & Co. KGaA, Lenzkirch (DE)

( * ) Notice: Subject to any disclaimer, the term of this patent is extended or adjusted under 35 U.S.C. 154(b) by 538 days.

(21) Appl. No.: 15/631,433

(22) Filed: Jun. 23, 2017

(65) Prior Publication Data

US 2017/0367535 A1  Dec. 28, 2017

(30) Foreign Application Priority Data

Jun. 24, 2016  (DE) .......... 10 2016 007 668

(51) Int. Cl.
- *G01N 33/03* (2006.01)
- *G01N 27/22* (2006.01)
- *A47J 37/12* (2006.01)

(52) U.S. Cl.
CPC .......... *G01N 33/03* (2013.01); *A47J 37/1266* (2013.01); *A47J 37/1271* (2013.01); *G01N 27/221* (2013.01); *A47J 37/1285* (2013.01)

(58) Field of Classification Search
CPC .. A47J 37/1266; A47J 37/1271; G01N 33/03; G01N 33/28; G01N 27/221
See application file for complete search history.

(56) References Cited

U.S. PATENT DOCUMENTS

| | | | | |
|---|---|---|---|---|
| 5,818,731 A | * | 10/1998 | Mittal | A47J 37/1266 702/22 |
| 6,469,521 B1 | * | 10/2002 | Klun | G01N 27/221 324/658 |
| 6,600,306 B1 | * | 7/2003 | Pernot | A47J 37/1266 324/423 |

(Continued)

FOREIGN PATENT DOCUMENTS

EP  2712665  4/2014

OTHER PUBLICATIONS

Hydac Filtertechnik GmbH; FCU 1000 Serie FluidControl Unit—Betriebs- und Wartungsanleitung, [Apr. 12, 2007], URL: https://www.hydac.com/fileadmin/pdb/pdf/BUW00000000000000120097249A_0001.pdf [downloaded on Dec. 6, 2017], German Original, V. V 1.10, Doc. 3371346a/2007-12-03, pp. 1-64.

*Primary Examiner* — Nathaniel J Kolb
(74) *Attorney, Agent, or Firm* — Volpe and Koenig, P.C.

(57) ABSTRACT

For the monitoring of an oil situated in a tank 19, it is provided that an oil measurement device 1 be equipped with a rigid or flexible probe 2 such that, by the use of a pump 5 integrated in the oil measurement device 1, oil can be delivered out of the tank 19 via an inlet opening 3 at the proximal end of the probe 2 into a measurement chamber 4, which is connected to the probe, of the oil measurement device 1. Here, the oil measurement device 1 has a measurement sensor for determining the quality of oil situated in the measurement chamber 4, and the pump 5, in conjunction with the probe 2, is configured such that oil can be returned from the measurement chamber 4 to the inlet opening 3 and thus to the tank 19.

18 Claims, 3 Drawing Sheets

(56) References Cited

U.S. PATENT DOCUMENTS

| | | | | |
|---|---|---|---|---|
| 6,897,661 B2* | 5/2005 | Allen | ............ | G01N 27/221 |
| | | | | 324/663 |
| 8,287,182 B2* | 10/2012 | Muhl | ............ | G01N 33/03 |
| | | | | 324/698 |
| 2003/0155935 A1* | 8/2003 | Klun | ............ | G01N 33/03 |
| | | | | 324/664 |
| 2008/0196596 A1* | 8/2008 | Forrest | ............ | A47J 37/1219 |
| | | | | 99/408 |
| 2009/0252842 A1* | 10/2009 | Wang | ............ | A23L 3/32 |
| | | | | 426/231 |
| 2009/0309619 A1* | 12/2009 | Behle | ............ | G01N 33/03 |
| | | | | 324/698 |
| 2010/0172391 A1* | 7/2010 | Muhl | ............ | G01N 33/03 |
| | | | | 374/1 |
| 2011/0030486 A1* | 2/2011 | Hall | ............ | G01N 27/221 |
| | | | | 73/866 |
| 2013/0036916 A1* | 2/2013 | Burkett | ............ | A47J 37/1266 |
| | | | | 99/330 |
| 2013/0278276 A1* | 10/2013 | Behle | ............ | G01N 21/534 |
| | | | | 324/663 |
| 2015/0027205 A1* | 1/2015 | Brugger | ............ | A47J 37/1266 |
| | | | | 73/53.01 |
| 2015/0285777 A1* | 10/2015 | Baumann | ............ | G01N 27/24 |
| | | | | 73/64.56 |
| 2015/0374173 A1* | 12/2015 | McGhee | ............ | G01N 33/03 |
| | | | | 99/330 |
| 2016/0033463 A1* | 2/2016 | Robertson | ............ | A47J 37/1223 |
| | | | | 426/231 |
| 2017/0030880 A1* | 2/2017 | Behle | ............ | G01N 21/534 |
| 2017/0138883 A1* | 5/2017 | Lambert | ............ | G01N 27/06 |
| 2017/0176369 A1* | 6/2017 | Lambert | ............ | G05D 7/0617 |
| 2019/0383781 A1* | 12/2019 | Behle | ............ | G01N 33/03 |

\* cited by examiner

OIL MEASUREMENT DEVICE AND METHOD FOR MONITORING AN OIL SITUATED IN A TANK

INCORPORATION BY REFERENCE

The following documents are incorporated herein by reference as if fully set forth: German Patent Application No. 102016007668.2, filed Jun. 24, 2016.

BACKGROUND

The invention relates to an oil measurement device for determining and/or monitoring the temperature and/or the quality of oil situated in a tank.

The invention also relates to a method for monitoring oil situated in a tank. Here, depending on the application, various parameters may be of interest for the monitoring, such as for example the temperature and quality of the oil or for example the number and/or duration of heating cycles that the oil undergoes during use.

In the prior art, it is for example possible to find numerous household and/or catering devices which have tanks, in particular electrically heatable tanks, which are filled with liquid oil or grease during operation. In large kitchens in particular, use is made for example of positionally fixed deep fryers in which preferably continuous monitoring of the temperature of the liquid oil or grease and, at regular intervals, measurement of the quality of the oil or grease are necessary for food hygiene reasons.

With regard to deep fryers, conventional devices for example offer the possibility of monitoring the quality of the frying oil during operation. For this purpose, a return line is typically provided between a frying tank and a filter tank, with a sensor being provided either in the return line or in a branch from the return line in order to check the quality of the oil that is pumped back.

For deep fryers in particular, measurement systems are thus known from the prior art which have sensors which are installed in positionally fixed fashion in the wall of a tank which accommodates the oil or in a filter circuit of the oil which is connected to said tank.

Such measurement systems cannot be removed from the device without relatively great structural modifications. Therefore, such non-modular systems in particular do not offer the possibility of a measurement functionality as described in the introduction being retrofitted with little effort to existing deep fryers without fixedly installed sensors. With existing systems, such retrofitting is cumbersome and expensive and, in the case of these, there is also no provision made for monitoring multiple tanks simultaneously or in flexible fashion.

There is however an increased demand for specifically such retrofittability and flexible monitoring because, firstly, the demands with regard to the monitoring of food hygiene are ever-increasing and, secondly, high costs for retrofitting or new procurement of devices must be avoided for economic reasons.

Typical processes which influence the quality of the oil, or more specifically the quality of the mixture of liquid oil or grease and other substances situated therein, are the breakdown of oil molecules and the absorption of water. Both processes generally lead to a change in the electrical characteristics of the oil, in particular to an increase of the electrical permittivity $\in$ of the oil, which is also referred to as dielectric conductivity.

It is known that the quality of the oil, that is to say in particular the purity of the oil and the water content in the oil, can be inferred by a measurement of the permittivity $\in$ of the oil.

To be able to make reliable statements regarding the quality of the oil on the basis of a measurement of the permittivity $\in$, a parallel temperature measurement is however necessary because, in the event of a temperature increase, water evaporates out of the oil, and therefore reliable statements can be made only after the evaporation.

SUMMARY

The invention is based on the object of providing an oil measurement device which can be handled in flexible fashion and by which the quality of an oil situated in a tank, and preferably also the temperature thereof, can be easily monitored.

To achieve this object, one or more of the features of the invention are utilized. In particular, it is this provided according to the invention, in order to achieve the object in the case of an oil measurement device of the type described in the introduction, that the oil measurement device comprises a probe which has an inlet opening at its distal end, a measurement chamber, which can be filled with oil and which is connected to the probe, and a pump for delivering oil from the inlet opening to the measurement chamber being arranged at a proximal end of the probe, the oil measurement device having a measurement element for determining the quality of the oil, and the pump being designed for returning oil that has been inspected in the measurement chamber to the inlet opening.

In the case of this refinement according to the invention of the oil measurement device, it is advantageous that the oil measurement device provides all of the structure for extracting the oil for inspection from the tank, for inspecting said oil, and for subsequently returning said oil to the tank. Due to the autonomy of the oil measurement device, it is thus possible to dispense with relatively great structural modifications to the tank. It is thus also possible for the oil measurement device to be used flexibly on multiple tanks, whereby the usage characteristics of the oil measurement device are significantly improved. In particular, the oil measurement device can thus be retrofitted in modular fashion to existing devices with oil baths, in particular household or catering devices with heatable oil baths, without relatively great structural modifications thereto. In this way, in particular for existing devices, a reliable and inexpensive possibility is created for monitoring the oil during operation and acquiring and recording associated measurement data.

According to the invention, the measurement element for determining the oil quality may preferably be arranged in or on the measurement chamber. In this way, a compact design of the oil measurement device and a high level of measurement accuracy can be attained.

A further advantageous embodiment may provide that the pump is configured for returning inspected oil via the probe to the tank. It is thus possible to avoid a situation in which the oil level in the tank falls as a result of repeated extractions of oil for measurements and it is thus necessary to replenish oil. Furthermore, in this embodiment, there is no need to dispose of oil that has already been inspected.

To be able to arrange the oil measurement device for example on existing deep fryers without structural modifications thereto, or to be able to integrate the oil measurement device into said deep fryers, said oil measurement device is, according to the invention, of modular construction: the oil measurement device constitutes an autonomous module which is fully functional as soon as an energy supply is provided. This modularity of the system permits a transfer from one device to another without problems, that is to say modularity is to be understood in this context in the sense of a modular system. Due to its modular construction, the system can thus be integrated in flexible fashion into other devices without the need for relatively great technical modifications to be made to the device for this purpose.

Further advantages of the modular construction can be seen in the fact that an electronics unit which may be provided, and which is for example equipped with an operating display, does not have to be arranged in the region of the hot oil but can be adequately spaced apart from the oil tank such that it can be more effectively cooled and such that it can in particular be arranged in flexible fashion on the oil tank in accordance with individual requirements of the user.

One embodiment according to the invention of the oil measurement device furthermore permits static or quasi-static monitoring of the quality of an oil bath. Here, an oil bath may be understood to mean a container of a device which is filled with liquid oil or grease, in particular owing to heating of liquid oil or grease. The expression "static measurement" may be understood here to mean that the system is preferably operated on a positionally fixed device, whereas the expression "quasi-static measurement" may be understood to mean that the system is operated preferably on a device which is positionally fixed at least on an interim basis.

A measurement principle according to the invention provides that, to monitor the oil, firstly the temperature of the oil and secondly the quality of the oil are measured, specifically in each case outside the oil tank. To monitor the oil quality, the oil can thus be pumped cyclically, that is to say at time intervals interrupted by breaks, from the oil bath into the measurement chamber in order to be measured there, wherein, after measurement has been performed, the oil can be fed back to the oil bath. This measurement method is preferred according to the invention. If necessary, it is however also possible for continuous monitoring of the oil quality to be realized by an oil measurement device or method according to the invention in the case of which the oil is continuously pumped through the measurement chamber and measured there.

According to the invention, the object may also be achieved by further advantageous embodiments as described below and in the claims.

In one advantageous refinement, it may be provided that the oil measurement device has an electronics unit. Said electronics unit may be used for actuating the pump and/or for determining the oil quality and/or for other monitoring and regulation of functions of the oil measurement device and/or for actuating a display with or without an input unit. It is thus possible for measurement and/or monitoring of the oil quality or oil temperature to be performed in controlled, in particular automated fashion by the electronics unit.

Here, the electronics unit is preferably situated outside the oil-filled tank. This refinement has the advantage that the electronics unit can be protected against excessive overheating by the hot oil and can in particular also be cooled more effectively.

A further embodiment according to the invention provides that the probe has one oil-transporting hose or pipe line as a common feed/return line or has dual hose or pipe lines, preferably as separate feed/return lines. The probe of the oil measurement device may thus have one or more probe hoses or one or more probe pipes. Here, the oil can be fed to the measurement cell via a feed line, preferably in the form of a hose or pipe line, and discharged from the measurement cell again via a return line. Alternatively, the feed and return lines may also be formed by one single hose or pipe line through which oil can be either fed to or discharged from the measurement cell alternately. It is thus possible in particular for the pump to return the oil to the oil bath of the device again via the return line.

The sampling can thus be performed via a circuit in which oil is extracted from the tank and fed to the measurement chamber via a feed line and said oil is subsequently fed back to the tank via a return line. Alternatively, the pump of the oil measurement device may also firstly feed the oil to the measurement chamber via a hose or pipe line and subsequently return said oil to the oil tank via the same hose or pipe line by a reversal of the pump direction.

It is thus possible according to the invention for the probe to be of flexible or rigid form. The probe may furthermore be configured for feeding and returning oil between the inlet opening and the measurement chamber. In particular, the probe may be in the form of an immersion probe. It is advantageous here that the depth of the extraction point of oil in the tank can be set by the immersion depth of the probe.

Depending on the application, it is possible by the embodiment of the oil measurement device with a rigid probe for the positioning capability thereof in the tank to be improved, whereas a flexible form of the probe may be advantageous if the probe is intended to be variably positionable in relation to the proximal components, for example of the pump. The embodiment as an immersion probe has the advantage that, in particular, a floating mounting of the probe in the oil-filled tank can be possible, and/or that the probe can preferably be configured for extracting oil from a defined depth of the tank.

To prevent a blockage of a probe pipe or of a probe hose, or some impairment of the measurement chamber, it may be provided according to the invention that the probe has a filter, preferably a filter arranged at the distal end of the probe, which filters the oil for inspection before said oil enters the measurement chamber.

A further refinement according to the invention provides that, in the region of the distal end of the probe, there is arranged a distal temperature sensor. By the use of said sensor, the temperature of the oil can be determined directly in the tank, and it is thus possible for a time point suitable for a measurement of the oil quality to be selected in particular in automated fashion. For this purpose, it is preferably possible for an electronics unit, in particular the electronics unit already mentioned further above, to be configured for reading out the distal temperature sensor and/or for cyclically and/or continuously monitoring the oil temperature. It is thus for example possible, in the presence of an insufficiently high temperature, for the oil measurement device to commence the delivery of oil into the measurement chamber only when a preset minimum temperature has been reached.

A further development of this specific refinement provides that a distal temperature sensor is in the form of a thermocouple. It is thus advantageous that commercially available, highly precise and inexpensive sensors can be used.

It may additionally or alternatively also be provided that a distal temperature sensor is arranged adjacent to an oil-transporting line. Here, it is particularly advantageous if the distal temperature sensor is arranged in the immediate vicinity of, in particular in heat-conducting contact with, an oil-transporting line and/or in the region of the inlet opening (3). By the use of these refinements, it is particularly easily possible for the oil temperature in the tank to be acquired with high accuracy, wherein the temperature sensor does not necessarily need to be in direct contact with the oil for this purpose.

A further embodiment of the invention provides for electrically measuring, in particular capacitively measuring, the permittivity of oil situated in the measurement chamber as a measure for the oil quality to be provided, and/or that the electronics unit is configured for acquiring the measured oil quality. In particular, according to the invention, a coaxial sensor for capacitive measurement in the measurement chamber may be provided. As already mentioned in the introduction, the measurement of the permittivity of oil constitutes a routine and well-established method for determining the oil quality. A highly precise measurement of the oil quality is thus easily possible, wherein only very small amounts of oil need to be extracted from the tank for this purpose.

A further development of this electrical measurement of the oil quality provides that the oil measurement device has a proximal temperature sensor for acquiring the oil temperature. Said proximal temperature sensor may for example be arranged in the immediate vicinity of the measurement chamber, preferably in heat-conducting contact with the measurement chamber, and/or in the measurement chamber. Here, the electronics unit may preferably be configured for reading out the proximal temperature sensor. Through the provision of the oil temperature prevailing in or in the vicinity of the measurement cell, it is thus possible to achieve an even more precise measurement of the permittivity and thus of the oil quality, because the not inconsiderable temperature dependency of the electrical permittivity of the oil in the measurement chamber can be taken into consideration in the interpretation of the measurement data.

A refinement of the invention which is particularly easy to handle provides that the proximal components, that is to say the measurement chamber, the pump, the sensor for determining the quality of the oil and any electronics unit that may be provided and preferably a proximal temperature sensor, are combined in or on a common housing. It is thus possible for the oil measurement device to be provided in particular in the form of a portable handheld device with a probe that can be attached to the housing. Here, the combination of components in one housing permits efficient protection against damage, in particular as a result of contact with hot oil, and a compact design of the oil measurement device overall.

Based on this refinement, it may also be provided that a position of the probe relative to the position of a housing which accommodates the proximal components is variable. It is thus possible for the usage characteristics of the probe to be significantly improved, because the probe can be positioned independently of the housing, which may be advantageous for the use of the oil measurement device in differently configured tanks. In particular, it is thus possible for the inlet opening of the probe to be positioned in flexible fashion relative to the pump, which can significantly improve the operability of the probe.

A particularly simple and thus attractive refinement of the oil measurement device according to the invention is obtained if the pump is in the form of a peristaltic pump and/or if the pump is arranged between measurement chamber and inlet opening. Here, it may in particular also be provided that the pump direction of the pump is reversible. By the use of such refinements, it is for example possible for one single line in the form of a pipe or a hose to be utilized as feed line and return line for oil, which may be expedient in order to keep the structural outlay for the probe low.

Further advantages in the use of the oil measurement device are obtained if the electronics unit has a data memory for storing acquired measurement values and/or an interface, preferably a wireless interface. Here, it is particularly advantageous if the interface is configured for outputting acquired and/or stored measurement data. The interface may thus be formed with conventional signal transmitters/receivers, for example with connectors for cables or with a radio unit, for example in the form of an RF transmitter. In particular, the interface may also have an operable display.

With an electronics unit configured in this way, it is thus possible for measurement values that have been recorded over relatively long time periods to be stored in the device and retrieved by a user, that is to say output to the user, via the interface at suitable time points, for example in order to be able to further process the data or merely for the purposes of documenting measurement data. A wireless interface offers the advantage here that the user does not need to move into the immediate vicinity of the oil measurement device in order to retrieve such data from the oil measurement device.

The efficiency and accuracy of the measurement of the oil quality in the measurement chamber may be further improved according to the invention through the provision of an apparatus for detecting and/or displaying the fill level of the oil in the measurement chamber, the electronics unit preferably being a constituent part of said apparatus. It is thus possible, for example, for the fill level of the oil in the measurement chamber to be acquired down to a minimum fill level, proceeding from which a measurement of the oil quality can be considered to be meaningful, either purely optically from the outside or by use of electronic sensors. Furthermore, by use of the fill level display, it is for example also possible for air bubbles in the measurement chamber, which could falsify a measurement, to be detectable.

Due to the simple implementation, a particularly preferred embodiment provides that the oil measurement device has means for detecting the fill level of the oil in the measurement chamber by monitoring the capacitive behavior of the measurement chamber. It may additionally or alternatively also be provided that the electronics unit is configured for starting a preferably capacitive measurement of the oil quality after detection of a minimum fill level of the oil in the measurement chamber. It is thus possible in a particularly simple manner, preferably using means already provided for measuring the oil quality, for the fill level of the oil in the measurement chamber to be detected and thus for a suitable time point for the starting of a measurement by use of the oil measurement device to be determinable.

A further advantageous refinement of the invention provides that the oil measurement device has a switching valve at which at least one further probe according to the invention can be arranged, in particular reversibly arranged. Here, at least one pump and at least one measurement chamber may be connected to the switching valve. It is thus possible in particular for oil from multiple probes to be deliverable or delivered by one common pump into one common measurement chamber. Furthermore, it may also be provided that the switching valve provides for reading out distal temperature sensors, which are integrated in the probes, via an electronics unit of the oil measurement device. The attachable probes may thus also be configured as temperature sensors without oil-delivering characteristics. By use of these refinements, it is thus possible for the flexible use of an oil measurement device according to the invention to be further improved.

Further improvements in the usage characteristics of the oil measurement device may be achieved according to the invention in that the probe, preferably the oil measurement device, is fastenable variably in terms of position, in particular removably, to a tank which accommodates an oil to be inspected. In particular, it may thus be provided that the probe, preferably the oil measurement device, can be used modularly on multiple tanks, whereby the possible field of use of the probe is expanded.

According to the invention, to achieve said object, the features of the independent method claim are provided. In particular, it is thus provided according to the invention, in order to achieve the object in the case of a method for measuring the quality of an oil situated in a tank as described in the introduction, that a part of the oil is extracted from the tank by a probe, preferably by a probe of an oil measurement device according to the invention, is measured and is subsequently returned to the tank via the same probe, the oil being delivered in particular by a pump. This method offers the crucial advantage that, for an inspection of quality, only very small amounts of the oil have to be extracted from the tank, such that it is possible in particular for dead volumes in lines, such as arise in the case of conventional systems, to be avoided. Furthermore, at most only marginal structural modifications to the tank are necessary in order to be able to implement such a method. By use of the method according to the invention, it is thus possible for an oil situated in a tank to be monitored, preferably in automated fashion, using simple technical means. It is thus possible for prescribed quality standards with regard to the oil to be adhered to during operation.

A further method according to the invention which is based on the method discussed immediately above provides that, to determine the oil quality of an oil situated in a tank, said oil is extracted from the tank, then measured in a measurement chamber connected to the probe, and subsequently returned to the tank again via the same probe. Here, it is advantageous if, preferably at a time before or during the oil quality measurement, the temperature of the oil is acquired at the distal end of the probe and/or at the proximal end of the probe, in the latter case preferably in the measurement chamber. This preferred method thus ensures that a high level of accuracy of the measurement can be achieved through the use of a measurement cell configured specifically for the measurement and/or by taking into consideration temperature effects in the oil tank and/or at the location of the measurement.

According to the invention, temperature monitoring may also serve for the monitoring of temperature cycles, wherein this method may be used in particular for monitoring frying cycles in the case of deep fryers: when foods for frying, in particular frozen goods, are placed into the deep fryer, a brief decrease of the oil temperature typically occurs, which thereafter increases to the operating temperature again, this being accompanied by an evaporation of water from the oil. The invention is based on the approach of recording and storing said decrease of the temperature by means of the temperature sensor, such that conclusions can be drawn regarding the duration and number of frying cycles from the determined data.

By use of a preferably cyclic or continuous measurement of the oil quality and of the temperature of the oil according to the invention with respect to time, it is thus possible, for example, for monitoring in particular of the following parameters to be achieved for a deep fryer: utilization of the deep fryer with respect to time, number and duration of frying cycles, operating duration of the deep fryer, and temperature fluctuations of the oil bath during the operation of the deep fryer.

Therefore, to achieve the stated object, the additional and/or alternative features of a second method are provided. In particular, it is thus provided according to the invention, in order to achieve the object in the case of a method for measuring the number and/or duration of heating cycles of an oil situated in a tank, as described in the introduction, that the temperature of the oil with respect to time is acquired by a probe, preferably by a probe of an oil measurement device according to one or more features of the invention related to an oil measurement device, and the number and duration of the heating cycles are calculated therefrom. Here, the acquisition of the temperature may preferably be performed cyclically with respect to time and/or continuously with respect to time. Here, continuous acquisition may be understood in particular to mean that measurement values are recorded continuously during the operation of the oil tank.

Furthermore, to determine the number and duration of the heating cycles, it may also be provided that, on the basis of undershot or overshot temperature threshold values and/or on the basis of measured rates of temperature change with respect to time, temperature drops or temperature rises are detected from which the number and/or duration of the heating cycles can be derived. In particular, it may also be provided here that the number and duration of the heating cycles can be or are stored for the purposes of further processing, preferably in the device utilized for the acquisition, and can be or are output therefrom.

It is particularly expedient here if in each case one oil measurement device according to the invention with probe according to the invention, in particular as described above or according to one of the patent claims directed to an oil measurement device, is used in the method according to the invention.

BRIEF DESCRIPTION OF THE DRAWINGS

The invention will now be described in more detail on the basis of exemplary embodiments but is not restricted to these exemplary embodiments. Further developments according to the invention will emerge from the combination of the features of at least one claim with the features of individual or several dependent claims and/or with the following description of a preferred exemplary embodiment, in particular in conjunction with the general description, the claims and the drawings.

In the drawings.

DETAILED DESCRIPTION OF THE PREFERRED EMBODIMENTS

Figure 1:
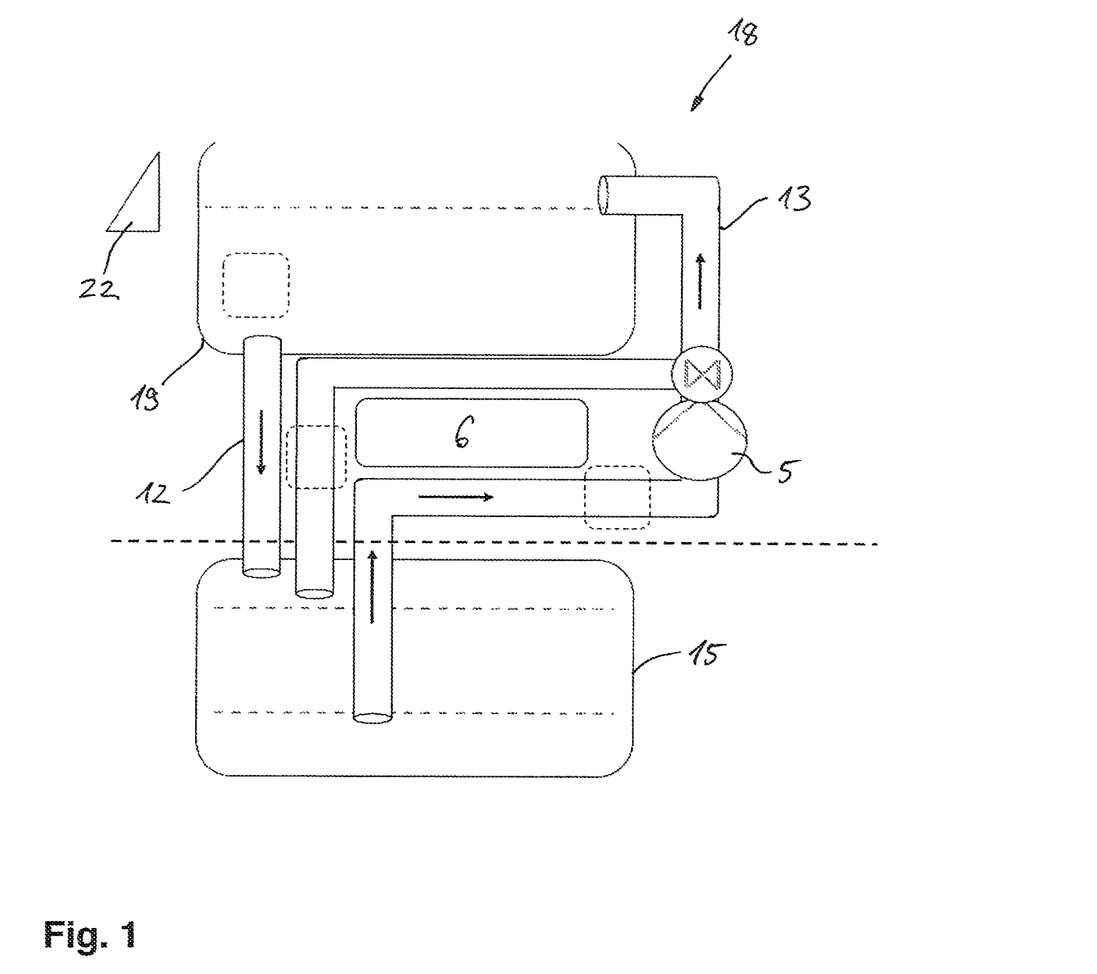
FIG. 1 shows the prior art relevant as a starting point of the invention, illustrated in a cross-sectional view of an oil-filled tank 19 to which an oil-circulating circuit together with pump 5 is connected, wherein a sensor arrangement for measuring the oil quality at various locations is fixedly installed in the circuit.

FIG. 1 shows a device 18 which is typical of the prior art, having a display with input unit 22 and having an oil-filled tank 19, in the case of which a circuit is formed by means of oil discharge and oil feed lines 12, 13 and a pump 5, which circuit circulates oil from the tank 19 through a filter 15 and back into the tank 19. As indicated by the boxes with dashed lines, for the purposes of monitoring the oil, sensors are typically fixedly installed at individual or several locations in the circuit or in the oil tank 19. For existing oil tanks with an oil-circulating pump 5, this means that such a sensor arrangement can be retrofitted only through relatively great modifications being made to the oil tank 19 and to the associated line system.

Figure 2:
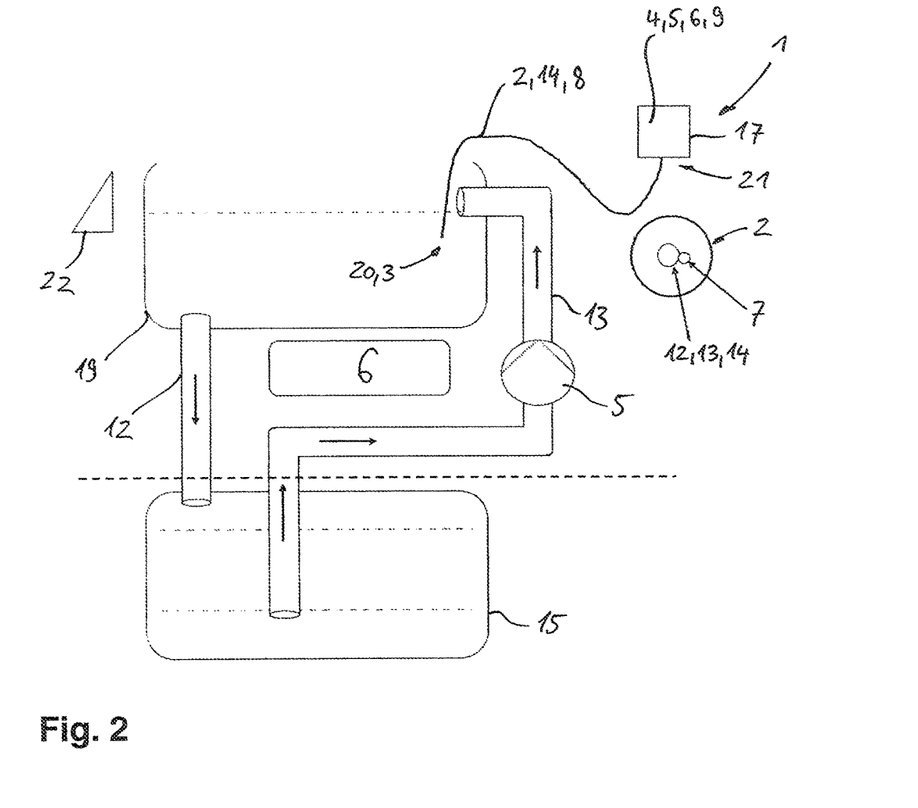
FIG. 2 shows an oil-filled tank 19 illustrated by way of example in a cross-sectional view, wherein a probe 2 according to the invention is immersed in the oil tank for the purposes of extracting oil from the tank and measuring said oil.

FIG. 2 illustrates how an oil measurement device 1 according to the invention can be used for monitoring an existing oil tank 19. For this purpose, it is merely necessary according to the invention for the probe 2 to be introduced into the oil, such that, via an inlet opening 3 at the distal end 20 of the probe 2, oil can be extracted from the tank and fed to a measurement chamber 4, which is connected to the probe, of the oil measurement device by a pump 5 integrated in the oil measurement device. This may in the simplest case be realized by a feed 12 and return line 13 in the form of a hose 14 which is integrated in or formed by the probe. Alternatively, it is also possible for dual hose or pipe lines 14, preferably in the form of separate feed/return lines 12, 13, to be formed in or by the probe. In particular, the pump may be operated such that it returns oil that has been inspected in the measurement chamber 4 to the oil tank 19 via a hose or pipe line 14. According to the invention, to measure the quality of the oil, measurement means are provided, which are not illustrated in FIG. 2 but which may be situated, in particular at the proximal end of the probe, in or at the measurement chamber 4. The oil measurement device may furthermore comprise an electronics unit 6 and a proximal temperature sensor 9, which are preferably accommodated in a housing 17 arranged at the proximal end 21 of the probe 2. Here, the electronics unit may preferably be configured for actuating the pump or for determining the oil quality. As shown by the detail in FIG. 2, it is possible according to the invention for a distal temperature sensor 7 to be arranged, in particular adjacent to an oil-transporting line 14, in or on the probe 2, wherein an arrangement in the region of the distal end 20 of the probe 2 is preferred. This temperature sensor may in particular be in the form of a thermocouple. Through the design of the oil measurement device with a compact and lightweight housing 17 and with a probe 2 that is movable independently thereof, it is possible in particular, as indicated in FIG. 2, for a position of the probe 2 relative to the position of the housing 17 to be varied, and also for the oil measurement device 1 as a whole to be fastened variably in terms of position, in particular removably, to the oil tank 19. In this way, the handling of the oil measurement device 1 is significantly improved.

Figure 3:
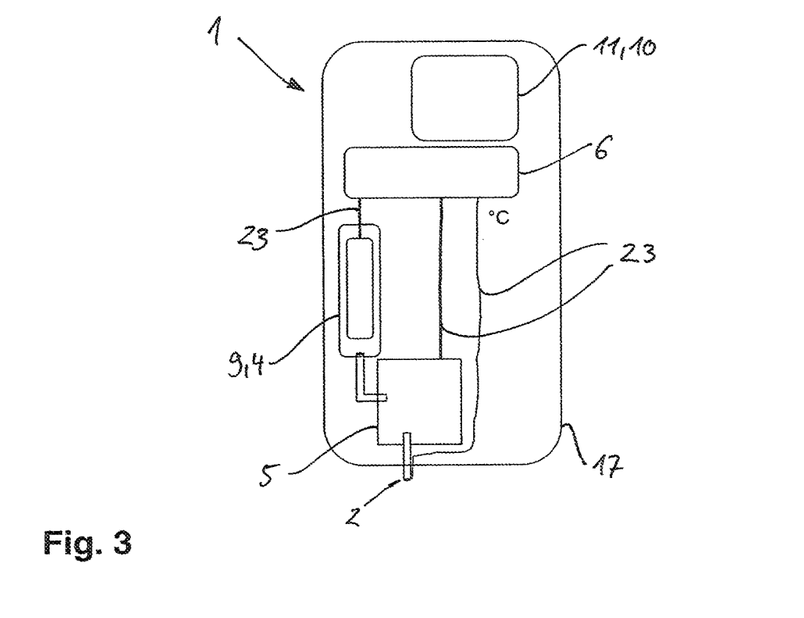
FIG. 3 shows a highly schematic view of a housing 17 of an oil measurement device 1 according to the invention with components typical for the invention contained therein.

FIG. 3 shows a schematic view of a housing 17 of an oil measurement device 1 according to the invention: as indicated by the reference designations, a housing of this type and thus the oil measurement device may comprise a measurement cell 4, a pump 5, an interface 1 and an electronics unit 6, wherein the electronics unit 6 may be connected as shown to the other components via control and supply lines 23. In particular, it is thus possible for the electronics unit to be configured for reading out and/or controlling the measurement cell 4, and/or for reading out and/or controlling distal and/or proximal temperature sensors 6, 7 and/or an interface, for example a wireless RF interface, and/or for acquiring a measured oil quality. It is thus possible for the oil measurement device 1 to also have a device or sensor for electrically measuring, in particular capacitively measuring, the permittivity of oil situated in the measurement chamber 4. Here, to achieve even greater measurement accuracy, it is preferable for an additional proximal temperature sensor 9 to be provided which, as shown in FIG. 2, acquires a temperature in particular in the immediate vicinity of the measurement chamber and/or in the measurement chamber 4. A very compact structural form of the housing 17 overall can be achieved if the pump 5 is in the form of a peristaltic pump. Further improvements of the oil measurement device 1 are achieved if, as illustrated in FIG. 3, the electronics unit 6 has a data memory 10 for storing acquired measurement values and/or an interface 11, preferably a wireless interface 11. It is thus possible for measurement data to be temporarily stored, and output for further processing, in a very simple manner. The oil measurement device 1 may also, in the region of the measurement chamber 4, have an apparatus (not illustrated in any more detail in FIG. 3) for detecting and/or displaying the fill level of the oil in the measurement chamber 4, wherein the electronics unit is preferably a constituent part of said apparatus. This apparatus may thus be provided for example in the form of a simple viewing window on the measurement chamber that can be filled with oil, as a signal lamp, or for example as an indicator in a display 22 of the oil measurement device 1. Provision may furthermore also be made for the oil measurement device 1 to have a sensor for detecting the fill level of the oil in the measurement chamber 4 by a capacitive measurement, wherein, in addition or alternatively, the electronics unit 6 may also be configured for starting a preferably capacitive measurement of the oil quality after detection of a minimum fill level of the oil in the measurement chamber 4. As illustrated in FIG. 3, this functionality is made possible by the control and supply lines 23 which run between the individual components of the housing 17. The probe 2 may be reversibly attachable to the housing 17 or fixedly installed therewith. As indicated by FIG. 3, the pump 5 is preferably arranged between the measurement cell 4 and the probe 2.

Figure 4:
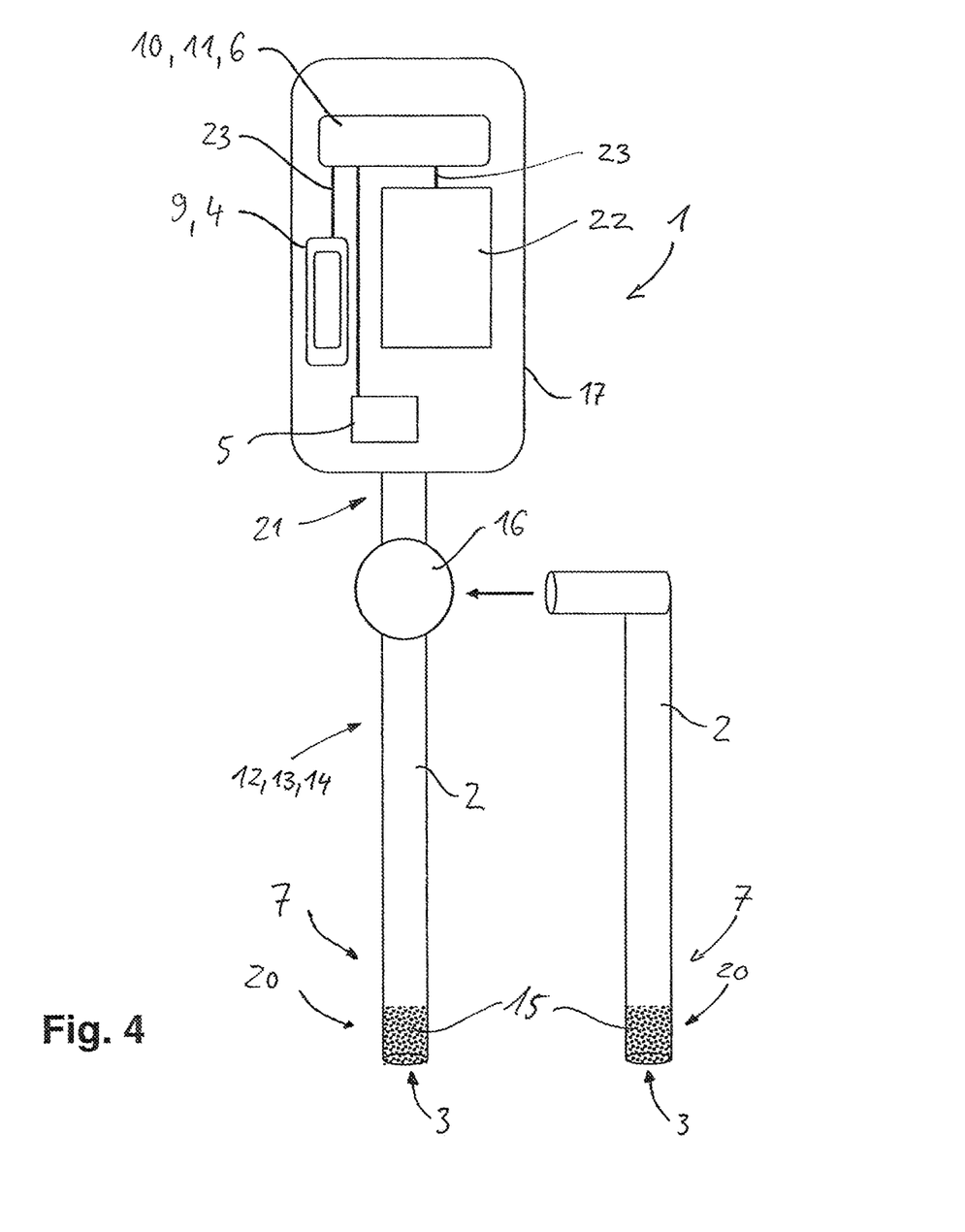
FIG. 4 is a schematic illustration of an oil measurement device 1 according to the invention with two probes 2 according to the invention, which are connectable by a switching valve 16.

Finally, FIG. 4 shows how, with the aid of a switching valve 16, further probes 2 according to the invention can be connected to or arranged on the oil measurement device 1. The probes may each be equipped with distal temperature sensors 7 and filters 15 and have feed and return lines 12, 13 which are present in the form of hose or pipe lines 14, or said probes form such lines. The filter which filters the oil for inspection before said oil enters the measurement chamber may also be arranged within the housing 17, but is preferably arranged at the distal end 20 of the probe 2 as shown in FIG. 4. In the embodiment shown in FIG. 4, the housing 17 has, by way of example, at the proximal end 21 of the probe 2, an electronics unit 6 with data memory 10 and interface 11, a measurement cell 4 with integrated proximal temperature sensor 9, a pump 5 and a display 22 with input unit.

To monitor an oil situated in a tank 19, it is provided that an oil measurement device 1 be equipped with a rigid or flexible probe 2 such that, by the uses of a pump 5 integrated in the oil measurement device 1, oil can be delivered out of the tank 19 via an inlet opening 3 at the proximal end of the probe 2 into a measurement chamber 4, which is connected to the probe, of the oil measurement device 1. Here, the oil measurement device 1 has a measurement sensor for determining the quality of oil situated in the measurement chamber 4, and the pump 5, in conjunction with the probe 2, is configured such that oil can be returned from the measurement chamber 4 to the inlet opening 3 and thus to the tank 19.

LIST OF REFERENCE DESIGNATIONS

1 Oil measurement device
2 Probe
3 Inlet opening
4 Measurement chamber
5 Pump
6 Electronics unit
7 Distal temperature sensor
8 Line
9 Proximal temperature sensor
10 Data memory
11 Interface
12 Feed line
13 Return line
14 Hose or pipe line
15 Filter
16 Switching valve
17 Housing
18 Device
19 Oil tank
20 Distal end of the probe
21 Proximal end of the probe
22 Display with input unit
23 Control and supply lines

The invention claimed is:

1. An oil measurement device (1) comprising a probe (2) which has an inlet opening (3) at a distal end (20) thereof, a measurement chamber (4), which is fillable with oil and which is connected to the probe, a pump (5) for delivering oil from the inlet opening (3) to the measurement chamber (4) arranged at a proximal end (21) of the probe (2), and a measurement sensor that determines a quality of the oil, wherein the pump (5) is configured to return oil that has been inspected in the measurement chamber (4) to the inlet opening (3) via the same probe.

2. The oil measurement device (1) as claimed in claim 1, further comprising an electronics unit (6) for at least one of actuating the pump (5) or for determining the oil quality.

3. The oil measurement device (1) as claimed in claim 2, wherein proximal components, including the pump (5), the measurement sensor for determining the quality of the oil and the electronics unit (6) are combined in or on a common housing (17).

4. The oil measurement device (1) as claimed in claim 3, wherein a position of the probe (2) relative to the position of a housing (17) which accommodates the proximal components of the oil measurement device (1) is variable.

5. The oil measurement device (1) as claimed in claim 2, wherein the electronics unit (6) includes at least one of a data memory (10) for storing acquired measurement values or an interface (11) for data communication.

6. The oil measurement device (1) as claimed in claim 2, further comprising an apparatus for at least one of detecting or displaying the fill level of the oil in the measurement chamber (4), with the electronics unit (6) comprising a constituent part of said apparatus.

7. The oil measurement device (1) as claimed in claim 1, wherein the probe (2) has a filter (15) which is adapted to filter the oil for inspection before said oil enters the measurement chamber (4).

8. The oil measurement device (1) as claimed in claim 1, wherein the probe (2) has a distal temperature sensor (7).

9. The oil measurement device (1) as claimed in claim 8, wherein the distal temperature sensor (7) comprises a thermocouple.

10. The oil measurement device (1) as claimed in claim 8, wherein the distal temperature sensor (7) is arranged adjacent to an oil-transporting line (8).

11. The oil measurement device (1) as claimed in claim 1, wherein the sensor electrically measures a permittivity of oil situated in the measurement chamber (4), or the electronics unit (6) is configured for acquiring a measured oil quality, or both.

12. The oil measurement device (1) as claimed in claim 1, further comprising a proximal temperature sensor (9) for acquiring the oil temperature, the proximal temperature sensor (9) being arranged in the immediate vicinity of the measuring chamber (4) or in the measurement chamber (4).

13. The oil measurement device (1) as claimed in claim 1, wherein the pump (5) comprises a peristaltic pump.

14. The oil measurement device (1) as claimed in claim 1, further comprising a fill level sensor for the oil in the measurement chamber (4) that utilizes a capacitive measurement, or the electronics unit (6) is configured for starting a capacitive measurement of the oil quality after detection of a minimum fill level of the oil in the measurement chamber (4), or both.

15. The oil measurement device (1) as claimed in claim 1, further comprising at least one further probe (2) that is arrangeable at a switching valve (16), such that oil from multiple probes (2) can be delivered into one said measurement chamber (4) by one said pump (5).

16. The oil measurement device (1) as claimed in claim 1, wherein the probe (2) is fastenable variably in terms of position, to a tank (19) which accommodates an oil to be inspected.

17. A method for measuring a quality of oil situated in a tank (19), comprising extracting a part of the oil from the tank (19) by using a probe (2), measuring a quality of the oil and subsequently returning the oil to the tank (19) via the same probe, wherein the oil is delivered by a pump (5).

18. The method for measuring an oil situated in a tank (19) as claimed in claim 17, further comprising measuring the oil quality in a measurement chamber (4) connected to the probe, and acquiring a temperature of the oil at least one of a distal end (20) or a proximal end (21) of the probe (2).

* * * * *